(12) United States Patent
Balakrishnan et al.

(10) Patent No.: US 9,924,735 B2
(45) Date of Patent: Mar. 27, 2018

(54) APPLICATION OF BETA ZEOLITE AS MULTI-TOXIN AND PESTICIDE BINDER IN ANIMAL FEED

(71) Applicant: Kemin Industries, Inc., Des Moines, IA (US)

(72) Inventors: Umesh Balakrishnan, Chennai (IN); Rajendra Moorthy, Madurai (IN)

(73) Assignee: KEMIN INDUSTRIES, INC., Des Moines, IA (US)

( * ) Notice: Subject to any disclaimer, the term of this patent is extended or adjusted under 35 U.S.C. 154(b) by 4 days.

(21) Appl. No.: 15/195,551

(22) Filed: Jun. 28, 2016

(65) Prior Publication Data

US 2016/0302447 A1 Oct. 20, 2016

Related U.S. Application Data

(63) Continuation-in-part of application No. 14/630,017, filed on Feb. 24, 2015, now abandoned.

(60) Provisional application No. 61/978,457, filed on Apr. 11, 2014.

(30) Foreign Application Priority Data

Feb. 26, 2014 (IN) .............................. 544/DEL/2014

(51) Int. Cl.
| | |
|---|---|
| *A23K 1/175* | (2006.01) |
| *A23K 20/28* | (2016.01) |
| *C01B 39/46* | (2006.01) |
| *A23K 50/15* | (2016.01) |
| *A23K 50/10* | (2016.01) |
| *A23K 50/75* | (2016.01) |
| *A23K 20/20* | (2016.01) |
| *C01B 39/48* | (2006.01) |

(52) U.S. Cl.
CPC .............. *A23K 20/28* (2016.05); *A23K 20/20* (2016.05); *A23K 50/10* (2016.05); *A23K 50/15* (2016.05); *A23K 50/75* (2016.05); *C01B 39/46* (2013.01); *C01B 39/48* (2013.01)

(58) Field of Classification Search
CPC ........ C01B 39/02; C01B 39/026; B01J 20/28; B01J 20/186; B01J 20/28083; A23K 20/28; A23K 50/00; A23K 50/10; A23K 50/15; A23K 50/75
See application file for complete search history.

(56) References Cited

U.S. PATENT DOCUMENTS

| | | | |
|---|---|---|---|
| 6,171,556 B1 | 1/2001 | Burk et al. | |
| 6,641,788 B1 | 11/2003 | Ogawa et al. | |
| 8,257,774 B2 | 9/2012 | Salado Font et al. | |
| 8,426,541 B2 | 4/2013 | Yiannikouris et al. | |
| 2005/0106267 A1 | 5/2005 | Frykman et al. | |
| 2009/0155380 A1* | 6/2009 | Hamon | A23K 1/1756 424/618 |
| 2010/0254894 A1 | 10/2010 | Wang et al. | |
| 2010/0310723 A1 | 12/2010 | Peterson | |
| 2011/0281018 A1 | 11/2011 | Schoeters et al. | |
| 2012/0315358 A1 | 12/2012 | Peterson | |
| 2013/0122143 A1 | 5/2013 | Davis et al. | |
| 2015/0237889 A1* | 8/2015 | Balakrishnan | A23K 1/1756 423/700 |

FOREIGN PATENT DOCUMENTS

| | | |
|---|---|---|
| WO | 9513127 A1 | 5/1995 |
| WO | 02052950 A1 | 7/2002 |
| WO | 02064502 A1 | 8/2002 |
| WO | 2005041657 A1 | 5/2005 |

OTHER PUBLICATIONS

Miazzo et al, Efficacy of Synthetic Zeolite to Reduce the Toxicity of Aflatoxin in Broiler Chicks, Poultry Science, (2000), 79:1-6.*
Harvey et al, "Efficacy of Zeolitic Ore Compounds . . . ", Avain Diseases,37:1, (Jan.-Mar. 1993) pp. 67-73.*
Burmanczuk et al, "Possible use of natural zeolites in animal production and environment protection", Journal of Elementaology, 20(4), (2014) pp. 803-811.*
International Searching Authority, "Search Report and Written Opinion," issued in connection with International Patent Application No. PCT/US15/17270, dated May 20, 2015, 5 pages.
International Searching Authority, "International Preliminary Report on Patentability," issued in connection with International Patent Application No. PCT/US15/17270, dated Mar. 21, 2016, 4 pages.
Ding et al., "Effect of Agitation on the Synthesis of Zeolite Beta and its Synthesis Mechanism in Abscense of Alkali Cations." Microporus and Mesoporus Materials, vol. 94, Elseiver, Apr. 24, 2006, pp. 1-8.
Peteri et al., "Ochratoxin degradation and adsorption caused by astaxanthin-producing yeasts," Food Microbiology, vol. 24, Elseiver, Aug. 17, 2006, pp. 205-210.
Mihalcik et al., "Screening acidic zeolites for catalytic fast pyrolysis of biomass and its components," Journal of Analytical and Applied Pyrolysis, vol. 92, Elsevier, Jan. 1, 2011, pp. 224-232.
P .M. Barata-Rodrigues et al., "Structured carbon adsorbents from clay, zeolite and mesoporous aluminosilicate templates," Carbon, vol. 41, Pergamon, Jan. 1, 2003, pp. 2231-2246.
Tamer, Nadir Hakan, "Synthesis and Characterization of Zeolite Beta". Jul. 1, 2006.
Camblor et al., "Synthesis in fluoride media and charterisation of aluminosilicate zeolite beta," Journal of Materials Chemistry, vol. 8, No. 9, Jan. 1, 1998, pp. 2137-2145.

* cited by examiner

*Primary Examiner* — David M Brunsman
(74) *Attorney, Agent, or Firm* — Nyemaster Goode

(57) ABSTRACT

The present invention relates to the application of beta zeolite in either a $NH_4^+$ or $H^+$ form to animal feed as a toxin binder, wherein the beta zeolite is effective at binding pesticides commonly present in animal feed.

5 Claims, 10 Drawing Sheets

APPLICATION OF BETA ZEOLITE AS MULTI-TOXIN AND PESTICIDE BINDER IN ANIMAL FEED

This application is a continuation-in-part of U.S. patent application Ser. No. 14/630,017, filed on Feb. 24, 2015. This application claims priority to Indian Application Serial No. 544/DEL/2014, filed on Feb. 26, 2014, and U.S. Patent Application Ser. No. 61/978,457, filed on Apr. 11, 2014, each of which is incorporated herein in its entirety by this reference.

BACKGROUND OF THE INVENTION

The present invention relates generally to toxin binders for animal feed applications and, more specifically, to the application of a novel microporous zeolite as a multi toxin binder in animal feeds.

Mycotoxins are invisible, odorless and cannot be detected by smell or taste, but can result in great economic losses at all levels of agricultural feed production and especially in animal production. Mycotoxins are secondary metabolites produced by filamentous fungi such as Fusarium, Aspergillus, and Penicillium prior to and during harvest, or during (improper) storage. Their toxic effects are very diverse depending upon the mycotoxins (Akande, K. E., Abubakar, M. M., Adegbola, T. A., and Bogoro, S. E. 2006. Nutritional and Health Implications of Mycotoxins in Animal Feeds: A Review. Pakistan Journal of Nutrition, 5: 398-403). In farm animals, mycotoxins have negative effects on feed intake, animal performance, reproductive rate, growth efficiency, and immunological defense as well as been carcinogenic, mutagenic, teratogenic, cause tremors or damage the central nervous system, hemorrhagic, as well as causing damage to the liver and kidneys. Mycotoxins are metabolized in the liver and the kidneys and also by microorganisms in the digestive tract. Therefore, often the chemical structure and associated toxicity of mycotoxin residues excreted by animals or found in their tissues are different from the parent molecule (Ratcliff, J. Aug. 16, 2002. The Role of Mycotoxins in Food and Feed Safety. Presented at Animal Feed Manufacturers Association). Various mycotoxins may occur simultaneously, depending on the environmental and substrate conditions (Sohn, H. B., Seo, J. A., and Lee, Y. W. 1999. Co-occurrence of Fusarium Mycotoxins in Mouldy and Healthy Corn from Korea. Food Additives and Contaminants. 16: 153-158). Considering this synergic effect, it is very likely, that animals are exposed to mixtures rather than to individual compounds. Field studies have shown that more severe toxicosis in animals can result from the additive and synergistic effects of different mycotoxins (Ratcliff J., 2002. The role of mycotoxins in food and feed safety. Presented at AFMA (Animal Feed Manufacturers Association) on 16 Aug. 2002). The problem of mycotoxins does not just end in animal feed or reduced animal performance; many become concentrated in meat, eggs and milk of animal and can pose a threat to human health. There is an increasing concern about levels of mycotoxins in human foods, both from vegetable origin and animal origin.

Although there are geographic and climatic differences in the production and occurrence of mycotoxins, exposure to these substances is worldwide. Mycotoxins are estimated to affect as much as 25 percent of the world's crops every year (Akande K. E., Abubakar M. M., Adegbola T. A. and Bogoro S. E. 2006. Nutritional and Health Implications of Mycotoxins in Animal Feeds: A Review. Pakistan Journal of Nutrition. 5 (5): 398-403). Most countries have stringent regulations on mycotoxin levels in feed and the main goal of agricultural and food industries are the prevention of mycotoxin contamination in the field. Management practices to maximize plant performance and decrease plant stress can decrease mycotoxin contamination substantially. This includes planting adapted varieties, proper fertilization, weed control, necessary irrigation, and proper crop rotation (Edwards, S. G. 2004. Influence of Agricultural Practices on Fusarium Infection of Cereals and Subsequent Contamination of Grain by Tricothecenes Mycotoxins. Toxicology Letters, 153: 29-35). But even the best management strategies cannot eliminate mycotoxin contamination in years favorable for disease development. Among the various mycotoxins identified especially affecting the agricultural and food industries, some occur significantly in naturally contaminated foods and feeds. It includes aflatoxin B1 (afla B1), ochratoxin A (OTA), zearalenone (zea), mycophenolic acid (MPA), cyclopiazonic acid (CPA), fumonisin B1 (fum B1), tricothecenes (T-2), deoxynivalenol (DON) and patulin (pat).

Afla B1, a metabolite of fungus Aspergillus flavus and Aspergillus parasiticus, is an extremely hepatotoxic compound that frequently contaminates poultry feeds at low levels (Ramos A. J., Hernandez E. 1996. In vitro aflatoxin adsorption by means of a montmorillonite silicate. A study of adsorption isotherm. Animal Feed Technology. 62: 263-269).

Another family of mycotoxins produced by Penicillium and Aspergillus genera is OTA, being the most potent toxin, adversely affects production parameters and the health of poultry. This mycotoxin is known to be a nephrotoxic, immunotoxic, carcinogenic, and teratogenic substance to a variety of animal species. Intestinal injuries including inflammation and diarrhea were seen on ingestion of OTA (Maresca M., Mahfoud R., Pfohl-Leszkowicz A and Fantini J. 2001. The mycotoxin ochratoxin A alters intestinal barrier and absorption functions but has no effect on chloride secretion. Toxicology and Applied Pharmacology. 176: 54-63).

Fusarium species which produces mycoestrogen zea, reported to activate estrogen receptors which results in functional alteration in reproductive organs. Swelling of the vent and increase in oviduct size could be asssociated with high levels of zea (Fink-Gremmels J, Malekinej ad H. 2007. Clinical effects and biochemical mechanisms associated with exposure to the mycoestrogen zearalenone. Animal Feed Science and Technology. 137:326-341.)

Penicillium roqueforti is one of the most important sources of MPA and it occurs predominantly in maize (Mansfield M. A., Jones A. D. and Kuldau G. A. 2008. Contamination of fresh and ensiled maize by multiple Penicillium mycotoxins. Department of Plant Pathology, the Pennsylvania State University, University Park 16802, USA. Phytopathology. 98: 330-6) and silage (Schneweis I., Meyer K., Hörmansdorfer S. and Bauer J. 2000. Mycophenolic Acid in Silage. Appl Environ Microbiol. 66: 3639-3641). Penicillium roqueforti, Penicillium rubrum, and Penicillium brevicompactum are associated with MPA production and found in both cattle and poultry feeds (Koteswara Rao V., Shilpa P., Girisham S and Reddy S. M. 2011. Incidence of mycotoxigenic Penicillia in feeds of Andhra Pradesh, India. International Journal for Biotechnology and Molecular Biology Research. 2: 46-50). The mycotoxin MPA has strong immunosuppressive action, which occurs by blocking the conversion of Inosine-5-phosphate to guanosine-5-phosphate (Allison A. C. and Eugui E. M. 2000. Mycophenolate mofetil and its Mechanism of action. *Immunopharmacology.* 47: 85-118).

The mycotoxin CPA is also produced by fungi belonging to the genus *Aspergillus* and *Penicillium*. The co-occurrence of CPA with afla B1 is mainly due to the growth of *Aspergillus flavus* which produces both these toxins (Dilek H., Sukra S., Funda K H and Nesirin M. 2012. Natural contamination of Cyclopiazonic acid in dried figs and co-occurrence of aflatoxin. *Food control.* 23: 82-86). The CPA toxicity in poultry also causes pathological effects such as hyperemia and ulceration of the proventriculus, focal necrosis in the liver and spleen, lymphoid depletion of the bursa of fabricius, weight loss and changes in relative organ weight (Gentles A., Smith E. E., Kubena L. F., Duffus E., Johnson Paul., Thompson J., Harvey R. B and Edrington T. S. 1999. Toxicological evaluations of Cyclopiazonic acid and Ochratoxin A in broilers. *Poultry science.* 78: 1380-1384).

Fum B1, a toxic compound was reported to be produced by *Fusarium moniliforme* (Gelderblom, W. C. A., Jeskiewicz, K., Marasas, W. F. O., Thiel, P. G., Horak, R. M. m Vleggaar, R., and Kriek, N. P. J. 1988. Fumonisins-novel, mycotoxins with cancer promoting activity produced by *Fusarium moniliforme. Appl. Environ. Microbiol.* 54: 1806-1811). The effects of this toxin includes rickets and immunosuppression in poultry (Norred, W. P. 1993. Fumonisins mycotoxins produced by *Fusarium moniliforme. J. Toxicol. Environ. Health.* 38:309-328). However the ill effects of this toxin were noted in other animal species also. Fum B1 was also reported to co-occur with afla B1 in Indian maize and poultry feeds (Prathapkumar H. Shetty and Ramesh V. Bhat. 1997. Natural Occurrence of Fumonisin B1 and Its Co-occurrence with Aflatoxin B1 in Indian Sorghum, Maize, and Poultry Feeds. *J. Agric. Food Chem.* 45: 2170-2173).

T-2 toxin produced by *Fusarium* fungi exerts toxic effects in poultry species also. The ill effect includes low performance in poultry production such as decreased weight gain, egg production, and hatchability. In addition to this inhibition of protein, DNA, and RNA synthesis, cytotoxicity, immunomodulation, cell lesions in the digestive tract, organs and skin, neural disturbances was also reported (Sokolovi M, et al. T-2 toxin incidence and toxicity in poultry. 2008. *Arh Hig Rada Toksikol* 59:43-52).

Patulin was reported to be isolated from fungus including *Penicillium* and *Aspergillus*. The effects of patulin were associated with alteration in renal function and inhibition of intestinal and renal ATPases (Puel O, Galtier P and Oswald I. P. 2010. Biosynthesis and Toxicological Effects of Patulin. *Toxins.* 2: 613-631).

The toxicity and clinical signs observed in animals when more than one mycotoxin is present in feed are complex and diverse. Mycotoxins are usually accompanied by other unknown metabolites which may have synergistic or additive effects. The ability of binders to alleviate the adverse effects of the several combinations of mycotoxins present naturally in feed on productivity and serum biochemical and hematological parameters remains yet to be explored.

Practical methods to detoxify mycotoxin contaminated grain on a large scale and in a cost-effective manner are not currently available. At present, one of the more promising and practical approaches is the use of adsorbents. However, several adsorbents have been shown to impair nutrient utilization (Kubena, L. F., Harvey R. B., Phillips T. D., Corrier D. E., and Huff W. E. 1990 Diminution of aflatoxicosis in growing chickens by the dietary addition of hydrated sodium calcium aluminosilicate. *Poult. Sci.* 69:727-735) and mineral adsorption (Chestnut, A. B., Anderson P. D., Cochran M. A., Fribourg H. A., and Twinn K. D. 1992. Effects of hydrated sodium calcium aluminosilicate on fescue toxicosis and mineral absorption. *J. Anim. Sci.* 70:2838-2846) and lack binding effects against multiple mycotoxins of practical importance (Edrington, T. S.; Sarr, A. B.; Kubena, L. F.; Harvey, R. B.; Phillips, T. D. 1996. Hydrated sodium calcium aluminosilicate (HSCAS), acidic HSCAS, and activated charcoal reduce urinary excretion of aflatoxin M1 in turkey poults. Lack of effect by activated charcoal on aflatoxicosis. *Toxicology letter,* 89: 115-122).

The use of mold inhibitors or preservation by acids can only reduce the amount of mold but does not influence the content of mycotoxins generated prior to treatment. If mycotoxins have been produced earlier they will not be affected in any form by mold inhibitors or acid mixtures, as they are very stable compounds. Thus these toxic compounds remain in the formerly infected commodity even if no further mold can be seen or detected. The most commonly used strategy of reducing exposure to mycotoxins is the decrease in their bioavailability by the inclusion of various mycotoxin binding agents or adsorbents, which leads to a reduction of mycotoxin uptake and distribution to the blood and target organs. Major advantages of adsorbents include expense, safety and the ease to add to animal feeds. Various substance groups have been tested and used for this purpose, with aluminum silicates, in particular clay and conventional zeolite minerals, as the most commonly applied groups.

Clay minerals have traditionally been supplemented to animal diets as multi-toxin binders. However, the degree of binding against high Log P value toxins such as ochratoxin A (OTA), mycophenolic acid and zearalenone was found to be low, possibly due to the charge and hydrophobicity of high Log P value mycotoxins. Hence the focus towards the use of alternate materials like zeolites (Dakovic, A., Tomasevic-Canovic, M., Dondur, V., Rottinghaus, G. E., Medakovic, V., and Zaric, S. (2005) Adsorption of mycotoxins by organozeolites. *Colloids Surfaces B: Biointerfaces* 46: 20-25), yeast cell wall products (Joannis-Cassan C, Tozlovanu M, Hadjeba-Medjdoub K, Ballet N, Pfohl-Leszkowicz A., (2011). Binding of zearalenone, aflatoxin B1, and ochratoxin A by yeast-based products: a method for quantification of adsorption performance. *J Food Prot.* 74:1175-85), molecular ion imprinting polymers (Yiannikouris A, Kwiatkowski A, Kudupoje M S and Matney C. Synthetic mycotoxin adsorbents and methods of making and utilizing the same. U.S. Pat. No. 8,426,541 B2) and functionalized material's (Dakovic, A., Tomasevic-Canovic, M., Dondur, V., Rottinghaus, G. E., Medakovic, V., and Zaric, S. (2005) Adsorption of mycotoxins by organozeolites. *Colloids Surfaces B: Biointerfaces* 46: 20-25) as toxin binders has been increased in recent past.

Zeolites which contain acidic sites at the surface with high surface area can bind organic molecules including toxins to a wide range of polarity. Both the $H^+$ form and $NH_{4+}$ form of beta zeolite, which contain ordered and disordered frameworks, coexist and there are three mutually intersecting channels. The framework structure has two types of 12 membered ring pores. The channel system of zeolite beta has pore diameters of 5.6×5.6 Å and 7.7×6.6 Å (Barcia, P. S., Silva, J. A. C., Rodrigues, A. E., (2005) Adsorption Equilibrium and Kinetics of Branched Hexane Isomers in Pellets of Beta Zeolite. *Microporous and Mesoporous Materials.* 79: 145-163.). The present invention relates to the binding efficacy of H beta zeolite (HBZ) against mycotoxins, including pesticides.

It is understood that agricultural products, such as corn and soybean meal, are used as raw material source for the production of animal feed. During the cultivation and storage period, various classes of pesticides are added to these materials in order to protect them from the attack of pests. Belden, J. B., Gilliom, R. J., Martin, J. D. and Lydy, M. J., (2006) Relative Toxicity and Occurrence Patterns of Pesticide Mixtures in Streams Draining Agricultural Watersheds Dominated by Corn and Soybean Production. Integrated Environmental Assessment and Management. 3:90-100. Such usage of pesticides contaminates the entire food chain. Consumption of pesticide contaminated materials can affect animal performance and may lead to mortality. Sachin Kumar, Sharma, A. K., Rawat, S. S., Jain. D. K. and Ghosh, S. Use of pesticides in agriculture and livestock animals and its impact on environment of India. *Asian Journal Of Environmental Science.* 8(1):51-57; Fleischli, M. A., Franson, J. C., Thomas, N. J., Finley, D. L. and Riley, W. 2004. Avian Mortality Events in the United States Caused by Anticholinesterase Pesticides: A Retrospective Summary of National Wildlife Health Center Records from 1980 to 2000. *Archives of Environmental Contamination and Toxicology.* 46, 542-550.

In addition to this, pesticides tend to accumulate in the animal products meant for human consumption such as meat, egg, milk, etc., which is a serious health and regulatory concern across the world. Aulakh, R. S., Gill, J. P. S., Bedi, J. S., Sharma, J. K., Joia, B. S. and Ockerman, H. W. 2006. Organochlorine pesticide residues in poultry feed, chicken muscle and eggs at a poultry farm in Punjab, India. *Journal of the Science of Food and Agriculture.* 86:741-744; Nasreddine, L., Massin, D. P. 2002. Food contamination by metals and pesticides in the European Union. Should we worry?. *Toxicology Letters.* 127: 29-41. Based on a pesticides analysis from feed samples, the most frequently observed pesticides are carbofuran, thiram, and chlorpyrifos. The levels of these pesticides varied between 40 ppb and 100 ppb.

The widely used adsorbent to protect animals from the effect of pesticides is activated charcoal (AC). Frazier, D. I. 2000. Avian toxicology. *In Manual of avian medicine,* eds. G. H. Olsen and S. E. Orosz, 228-63. New York: Mosby. At a high level of contamination (above ppm levels) where mortality is an issue, AC is used irrespective of its nutrient binding ability. However, continuous usage of AC can lead to performance issues due to binding of nutrients. Review of mycotoxin-detoxifying agents used as feed additives: mode of action, efficacy and feed/food safety. CFP/EFSA/FEEDAP/2009/01. Thus, there remains a need for a pesticide binder that overcomes the drawbacks and performance issues associated with AC.

SUMMARY OF THE INVENTION

The present invention consists of a toxin binder comprising beta zeolites. The beta zeolite disclosed herein has the potential to bind the mycotoxins, including but not limited to aflatoxin B1, ochratoxin A, zearalenone, mycophenolic acid, cyclopiazonic acid, Fumonisin B1, T-2 and patulin but also extend to other all fungal secondary metabolites present in animal feed. The beta zeolite is also effective at binding to pesticides present in animal feed, including but not limited to carbofuran, thiram, chlorpyrifos, deltamethrin, thiamethoxam, and atrazine.

BRIEF DESCRIPTION OF THE FIGURES

Figures 11, 12:
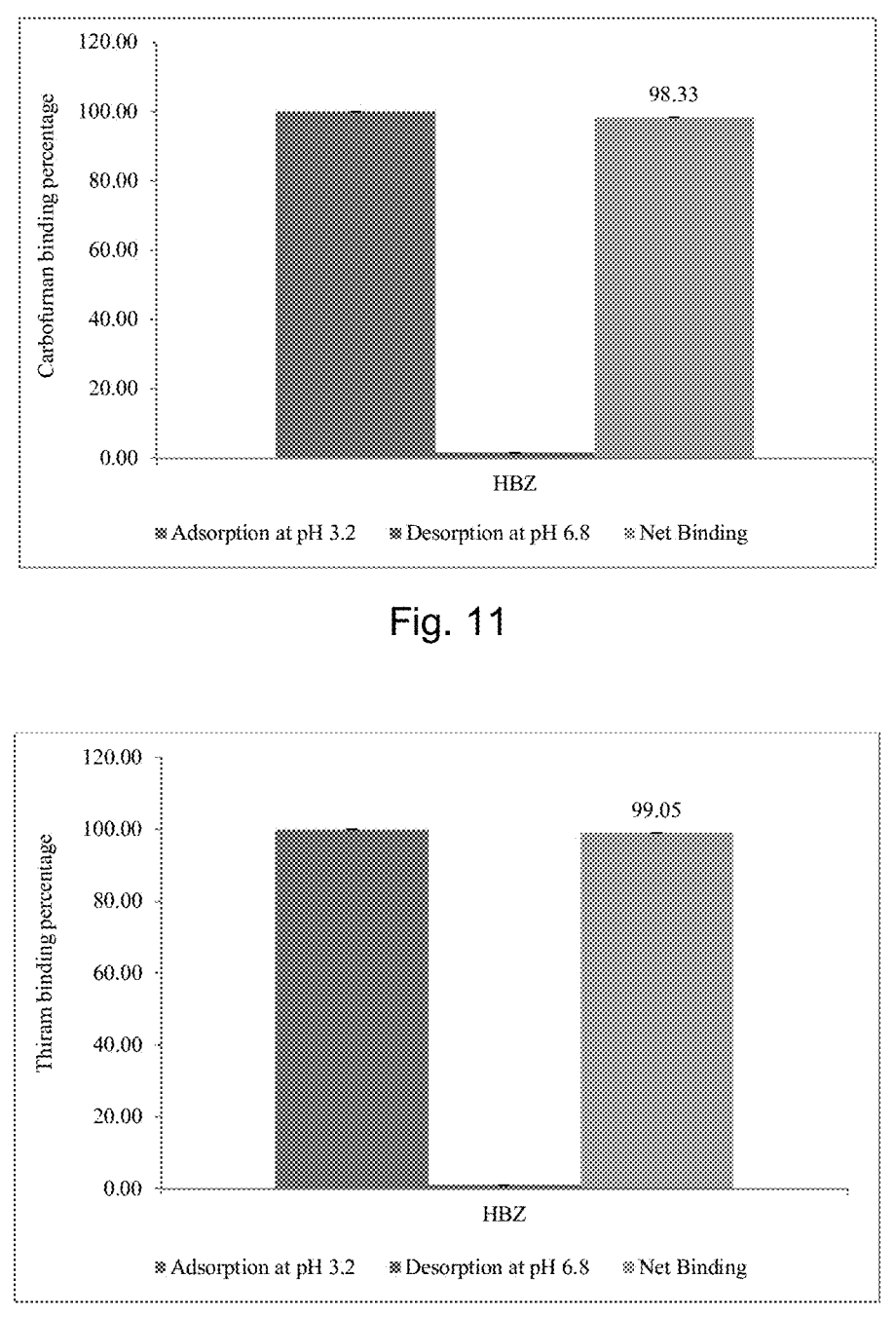

FIG. 11 is a chart on the in vitro binding efficacy of HBZ against carbofuran. Each experimental data represents mean binding+/−standard error (n=3).

FIG. 12 is a chart on the in vitro binding efficacy of HBZ against thiram. Each experimental data represents mean binding+/−standard error (n=3).

Figures 15, 16:
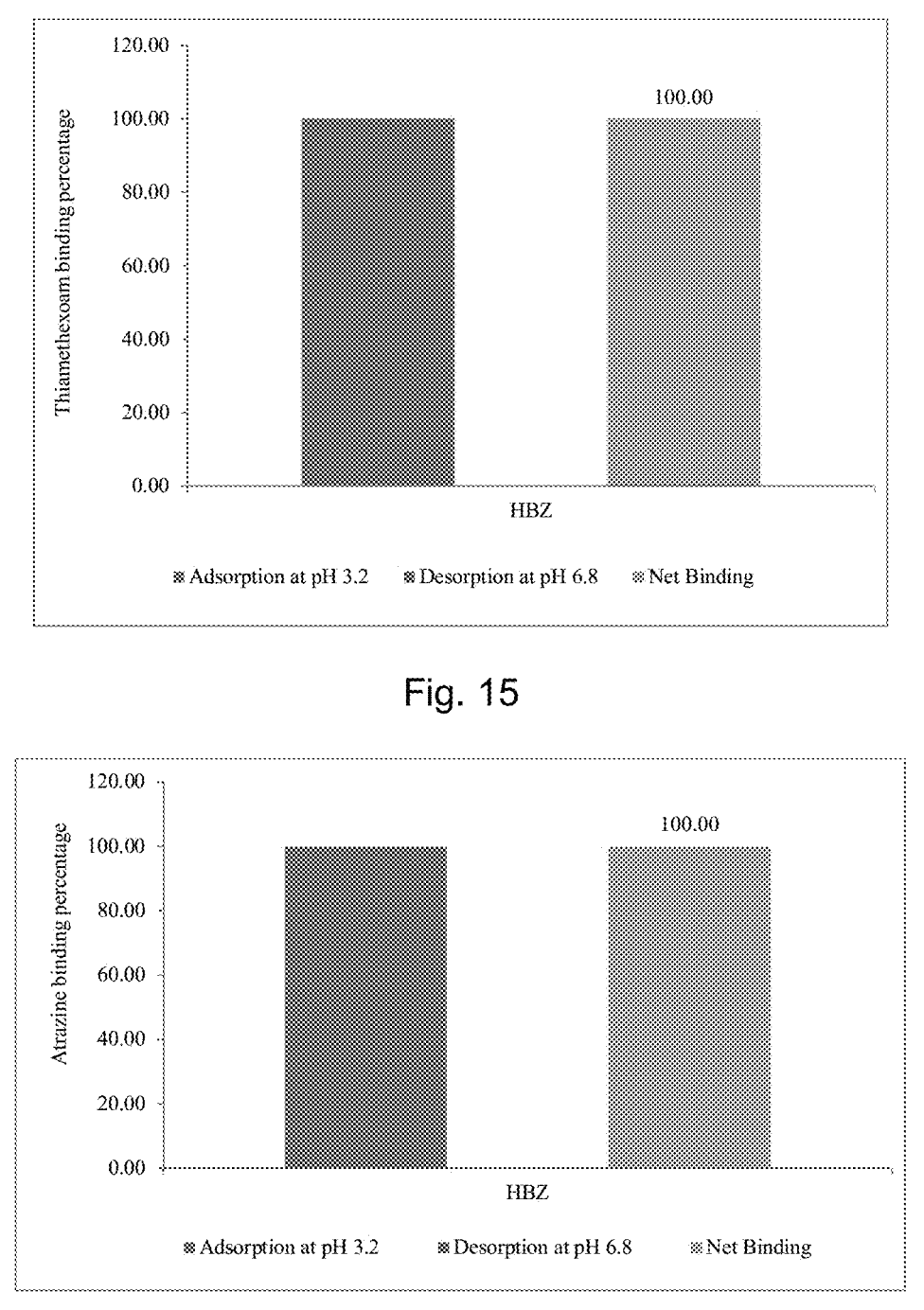

FIG. 15 is a chart on the in vitro binding efficacy of HBZ against thiamethoxam. Each experimental data represents mean binding+/−standard error (n=3).

FIG. 16 is a chart on the in vitro binding efficacy of HBZ against atrazine. Each experimental data represents mean binding+/−standard error (n=3).

DETAILED DESCRIPTION OF PREFERRED EMBODIMENTS

Figure 1:
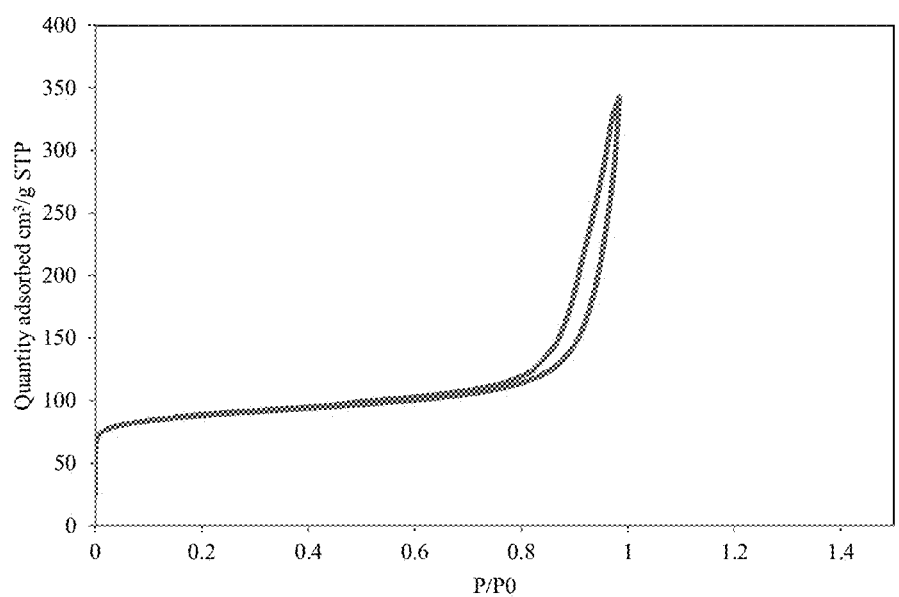
FIG. 1 is a chart of isotherm linear plot of HBZ.

Disclosed herein is a toxin binder comprising microporous zeolite materials having 12 membered ring systems. According to certain embodiments, the disclosed toxin binder comprises either a $NH_4+$ or $H+$ form of beta zeolite. In according to further embodiments, the disclosed beta zeolites have pore sizes in the range of about 1 to about 15 Å, but preferably about 5 Å. According to still further embodiments, disclosed beta zeolites have a Si/Al ratio in the range between about 10 to about 50, preferably around about 25. In yet further embodiments, disclosed beta zeolites have Lewis and Bronsted acidic sites at the surface as well as inside the pores. According to certain embodiments, the disclosed toxin binder is adapted for use as multitoxin binders in animal feed supplements. In further embodiments, the disclosed toxin binder is adapted for binding a mycotoxin, wherein the mycotoxin is selected from the group consisting of aflatoxin B1, ochratoxin A, zearalenone, mycophenolic acid, cyclopiazonic acid, fumonisin B1, T-2 and patulin and also extends to toxic secondary metabolites produced by fungus, bacterial exotoxins, bacterial endotoxins, ergot alkaloids and pesticides.

For purposes of the present disclosure:

The term "toxin" means, any substances including metabolites produced by microbial origin which are toxic in nature (e.g., Mycotoxins, bacterial endotoxins, Ergot alkaloids).

The term "pesticides" mean substances present in the animal feed capable of exerting cidal action against pests.

The term "binders" means, non-absorbable material which is capable of binding target molecules (e.g., Mycotoxins, bacterial endotoxins, ergot alkaloids).

The term "porous materials" refers to materials having pores in the framework.

The term "microporous materials" means, materials having a pore size of less than about 20 Å.

The term "pore size" means the measure of internal diameter of the channels present in zeolites.

The term "multitoxin binder" means, binder capable of binding more than one toxins.

The term "Lewis acidic sites" means, the presence of positive $Al^{3+}$ ion in the materials which has the tendency to accept the electrons.

The term "Bronsted acidic sites" means, the presence of positive $NH_{4+}$ ion in the materials which has the tendency to donate the electrons.

EXAMPLES

Example 1

Materials and Methods

The mycotoxins analyzed in the current invention were done through high performance liquid chromatography (HPLC). The mycotoxins used were obtained from Sigma-Aldrich, India. The separations were performed with a reverse phase C18 analytical column, Phenomenex, Luna C18 (250 mm×4.6 mm i.d., 5 μm particle size) at 1 ml/min flow rate. The mobile phase composition and detection wavelength used for quantification are set out in Table 1. The chromatographic system consisted of Shimadzu LC-20AD, equipped with fluorescence detector and diode array detector interfaced with LC solutions software (version 1.25).

TABLE 1

Mobile Phase composition and detector/wavelength used for quantification of toxins

| Serial No. | Name of the mycotoxin | Mobile Phase Composition | Detector/ wavelength |
|---|---|---|---|
| 1 | Afla B1 | Water:Acetonitrile = 70:30 | Fluorescent/Excitation wavelength: 365 Emission wavelength: 440 nm |
| 2 | OTA | 2% Aqueous glacial acetic acid: Acetonitrile = 40:60 | Fluorescent/Excitation wavelength: 333 Emission wavelength: 443 nm |
| 3 | Zea | 2% Aqueous glacial acetic acid: Acetonitrile = 40:60 | Fluorescent/Excitation wavelength: 274 Emission wavelength: 450 nm |
| 4 | MPA | Acetonitrile:Water adjusted to pH 3.0 with ortho-phosphoric acid = 60:40 | UV/284 nm |

TABLE 1-continued

Mobile Phase composition and detector/wavelength used for quantification of toxins

| Serial No. | Name of the mycotoxin | Mobile Phase Composition | Detector/ wavelength |
|---|---|---|---|
| 5 | CPA | Water:Methanol in ratio of 30:70 v/v containing 300 mg/l zinc sulphate | UV/284 nm |
| 6 | PAT | Water:Acetonitrile = 90:10 | UV/284 nm |
| 7 | Fum B1 | 0.1M phosphate buffer pH adjusted to 3.35 with orthophosphoric acid: Methanol = 30:70 | Excitation wavelength: 335 Emission wavelength: 440 nm |

Statistical Analysis.

All the analyses were carried out in multiple replicates. The statistical analysis was performed using ANOVA with STATGRAPHICS plus 5.1. The differences at $p<0.05$ were denoted with different superscripts and were considered significant.

In vitro binding method. The biphasic in vitro binding method involved adsorption at pH 3.2 (0.1 M citrate buffer) followed by desorption at pH 6.8 (0.1 M phosphate buffer). A known amount of binder (10 mg) was taken and was suspended in 1 ml of mycotoxin solution prepared in 0.1 M citrate buffer pH 3.2. The suspension was vortexed for 1 minute and was then kept in a shaking water bath at 40° C. for 45 minutes. After incubation the mixture was centrifuged (Eppendorf, 5810R) at 10000 rpm for 10 minutes at room temperature. The supernatant was removed and transferred into micro centrifuge tubes. The pellet was suspended with 1 ml of 0.1M phosphate buffer pH 6.8 and vortexed for 1 minute. The mixture was kept in shaking water bath at 40° C. for 45 minutes. After incubation the mixture was centrifuged at 10000 rpm for 10 minutes at room temperature. The supernatants were removed and transferred into micro centrifuge tubes. The supernatants were analyzed by HPLC as per the method described above and the net binding percentage (net binding=adsorption binding percentage−desorption binding percentage) was calculated.

Example 2

Beta zeolite was synthesized using a hydrothermal method having a molar composition of 30 TEAOH (tetra ethyl ammonium hydroxide)-50SiO$_2$—Al$_2$O$_3$-750H$_2$O and Si/Al ratio of 25. The material was synthesized based on the reported procedure (Ding L, Zheng Y, Zhang Z, Ring Z, Chen J. 2006. Effect of agitation on the synthesis of zeolite beta and its synthesis mechanism in the absence of alkali. *Microporous and Mesoporous Materials.* 94 1-8) of porous material synthesis which is widely used as catalyst in petrochemical industries. The synthesised material exchanged with 0.1M ammonium nitrate for 24 hours (NH$_4^+$ form). After Ammonium exchange, the product was filtered and calcinated at 550° C. for 12 hours (H$^+$ form). The final product so obtained is called H beta zeolite (HBZ) which was subsequently used for the further studies in this invention.

Example 3

The analyses were carried out to characterize the HBZ. The HBZ was characterized for BET surface area, BJH pore size using N$_2$ sorption analyzer (Quantachrome Autosorb)

and powder X-ray diffraction studies (pXRD, Rigaku diffractometer using Cu—Kα (λ=0.154 nm) radiation).

Figure 2:
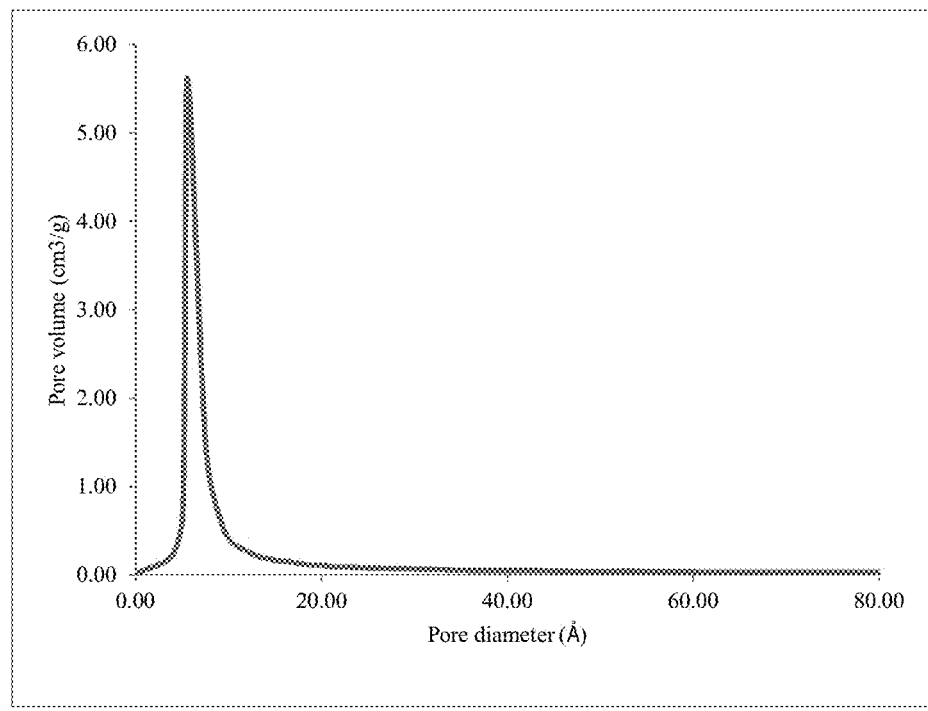
FIG. 2 is a chart of pore width analysis of HBZ by BJH method.

The nitrogen adsorption desorption isotherms and BJH pore size distribution HBZ are shown in FIGS. 1 and 2 and the results of surface area analysis by BET method are given in Table 2. The pore width (FIG. 2) was found to be 5.5 Å. These findings suggest that the smaller pore width of HBZ would have played a role in entrapping smaller molecules such as mycotoxins which could have led to a confinement effect (Li, C. 2004. Chiral synthesis on catalysts immobilized in microporous and mesoporous materials. *Catal. Rev.* 46: 419-492).

A narrow loop of type II isotherm was observed, which confirms the formation of a well-ordered microporous structure with uniform pore size distribution. The significant reduction in the amount of nitrogen adsorbed in the case of HBZ in both monolayer and the multilayer region confirms the formation of small pore size. It is also observed that the capillary condensation step which gives the direct measure of the pore diameter of the materials is shifted towards the low relative pressure for HBZ revealing a reduction in the pore diameter of the HBZ.

TABLE 2

BET surface area analysis of H-beta zeolite (HBZ).

| Materials | Surface area (m$^2$/g) |
|---|---|
| HBZ | 333 |

Figure 3:
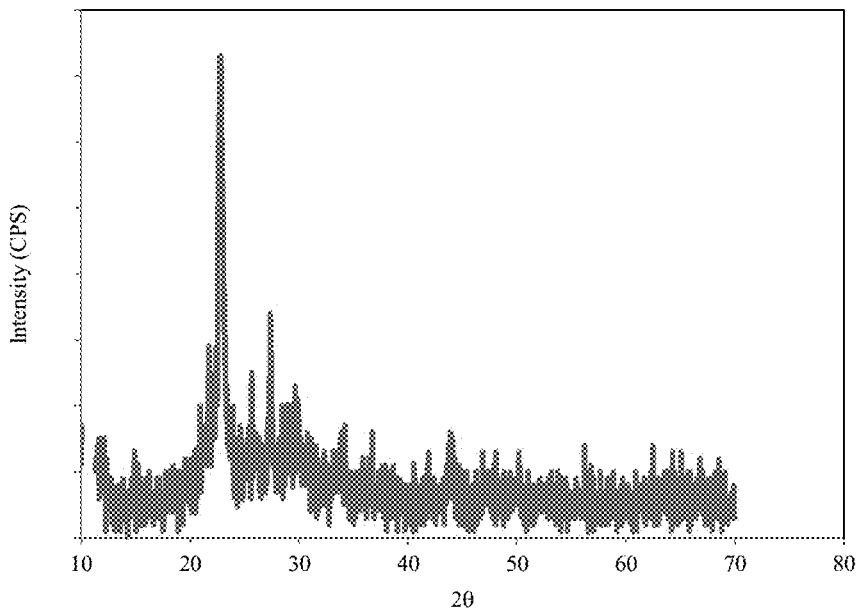
FIG. 3 is a chart of powder X-Ray Diffraction (pXRD) analysis of HBZ.

The material was further characterized by pXRD and the reflections are shown in FIG. 3. The reflections of HBZ at higher 2θ values between 21° and 23° confirms the formation of beta zeolite (Kang, Z., Zhang, X., Liu, H., Qiu, J., and Yeung, K. L. 2013. A rapid synthesis route for Sn-Beta zeolites by steam-assisted conversion and their catalytic performance in Baeyer-Villiger oxidation. *Chem. Eng. J.* 218: 425-432).

Example 4

Figure 4:
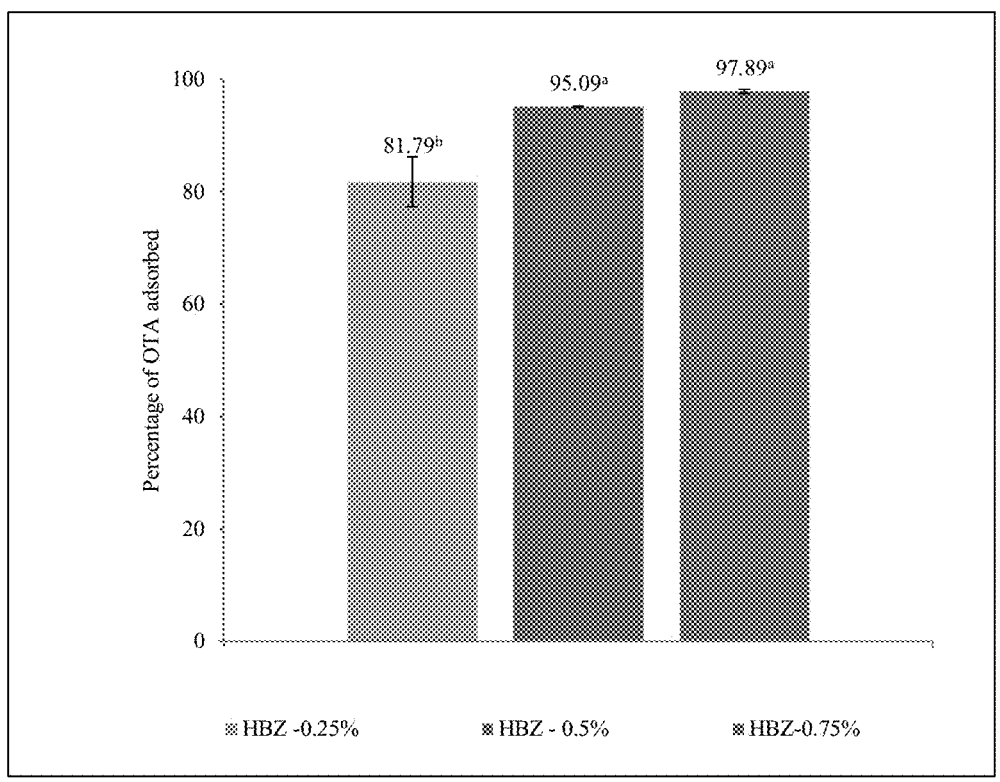
FIG. 4 is a chart of the binding efficacy of HBZ at three different concentration of the binder; each experimental data point represents mean net binding (mean+/−standard deviation (n=3)). Significant differences between the concentrations of HBZ were denoted with different letters in superscripts (ANOVA, $p<0.05$).

In vitro OTA binding was evaluated for HBZ by biphasic binding studies to find the least concentration necessary to adsorb/sequester the entire OTA used in the experiment. The procedure involves the suspension of HBZ: 0.75% (0.75 mg) in OTA solution (1 μg/mL prepared in citrate buffer pH 3.2) for 1 hour at 40° C. in shaking water bath. Subsequently the net binding of OTA was calculated as briefed in Example 1. Similarly, the evaluation at 0.25% and 0.5% were also done. FIG. 4 shows the influence of different concentrations of HBZ against OTA binding. High binding was observed at 0.5% and 0.75% HBZ. A dose related increase in binding was observed at 0.25% and 0.5% which was statistically significant ($p<0.05$, $n=3$). This indicates 0.5% adsorbent concentration was sufficient to bind the OTA concentration used in the experiment.

Example 5

Figure 5:
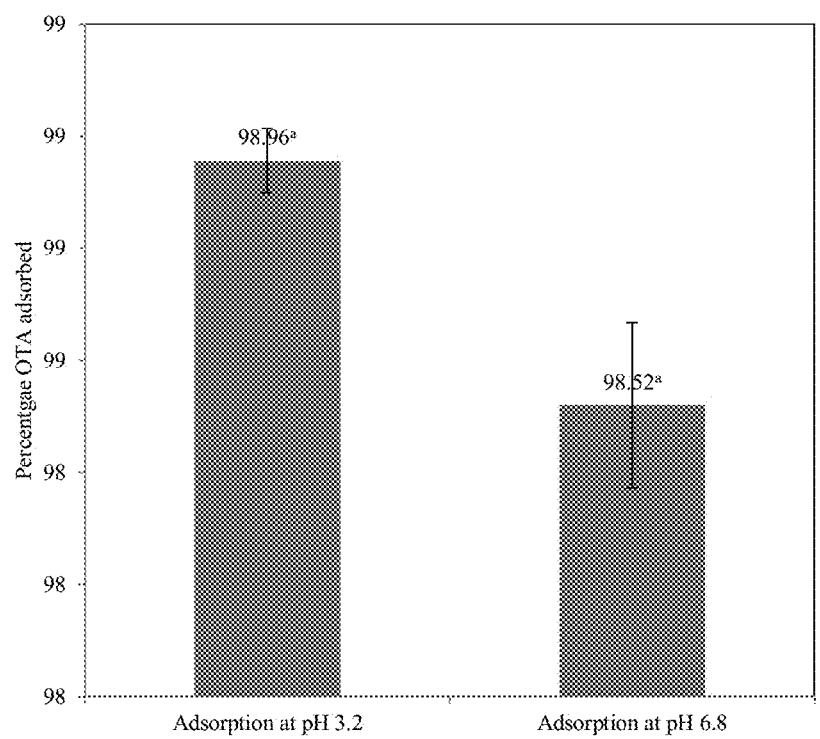
FIG. 5 is a chart on effect of acidic and near neutral pH on binding of HBZ against OTA. Each experimental data represents mean+/−standard error, n=3. Significant differences between the pH of HBZ were denoted with different letters in superscripts (ANOVA, $p<0.05$).

An experiment was conducted to evaluate the influence of pH on binding of OTA against HBZ. The OTA adsorption was evaluated individually at pH 3.2 and pH 6.8 as described in Example 1 with 1 μg/mL OTA and the results were shown in FIG. 5. HBZ exhibited maximum binding at pH 3.2 as well as pH 6.8 conditions. Statistically no difference in binding efficacy was observed for HBZ at pH 6.8 with respect to pH 3.2 ($p>0.05$, $n=3$). In most of the adsorption process, the effect of binding of mycotoxins from aqueous medium is highly dependent on pH, as pH affects the surface charge of adsorbents as well as the degree of ionization of toxins. This confirms HBZ could bind OTA irrespective of the ionization state (either ionized or unionized).

Figure 6:
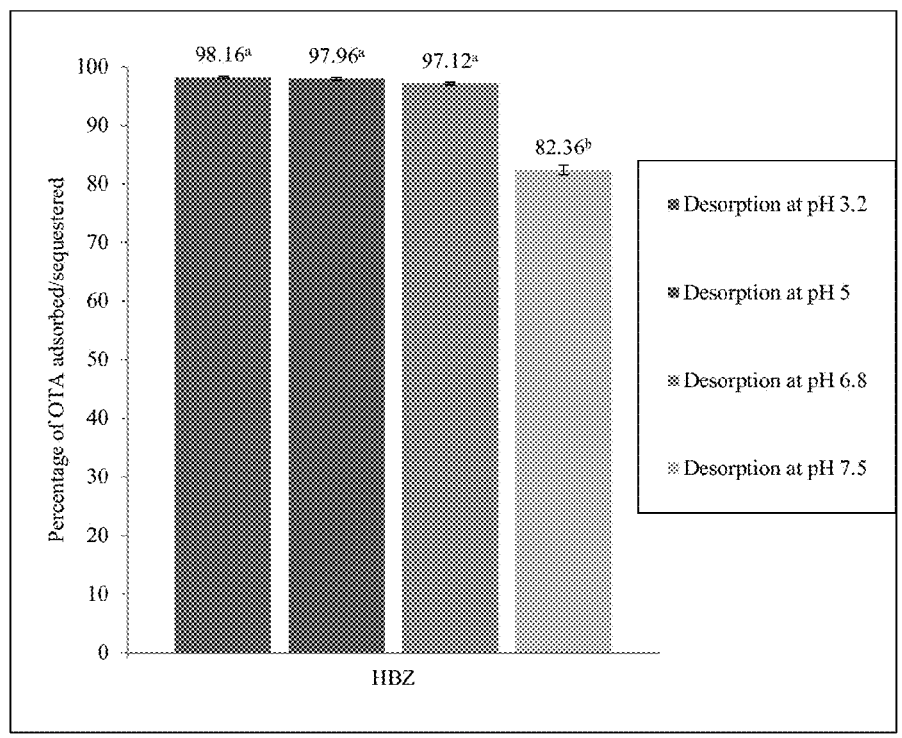
FIG. 6 is a chart on effect of different pH on adsorbed OTA in HBZ. Each experimental data represents mean+/−standard error, n=3. Significant differences between the pH were denoted with different letters in superscripts (ANOVA, $p<0.05$).

During the digestion process in monogastric animals, the pH of the food bolus changes to a large extent depending upon the gastro intestinal (GI) compartments i.e., from pH 6.5 (crop) to pH 3.0 (gizzard) and then to pH 7.5 (distal part of intestine, Fengying, G., Jie, G., Hui, R., and Guoqing, H. (2011) In Vitro Evaluating the Activities and Stabilities of the Multihydratases Produced by *Aspergillus Niger* Zju-Y1 in Simulated Poultry Digestive Tract pH Levels. *Procedia Eng.* 18, 405). Hence, the effect of pH simulating the pH of the GI tract was evaluated. OTA are adsorbed to adsorbents (HBZ) initially at pH 6.8 as per Example 1 and the pellets were sequentially evaluated for the desorption with 1 ml of pH 3.0, 5.0, 6.8 and 7.5 and the supernatants at each step were analyzed for OTA content. The residual OTA content adsorbed were calculated and the results were shown in FIG. 6. HBZ was observed with minimal (<5%) desorption at pHs (3.2, 5, 6.8) and around 16% desorption at pH 7.5 (FIG. 6). This study suggests that the bound OTA in HBZ remains almost intact as it travels through GI tract. These results and the findings suggests that the HBZ adsorbed OTA are almost stable on the entire pH range relevant to the GI tract of monogastrics.

Example 6

Figure 7:
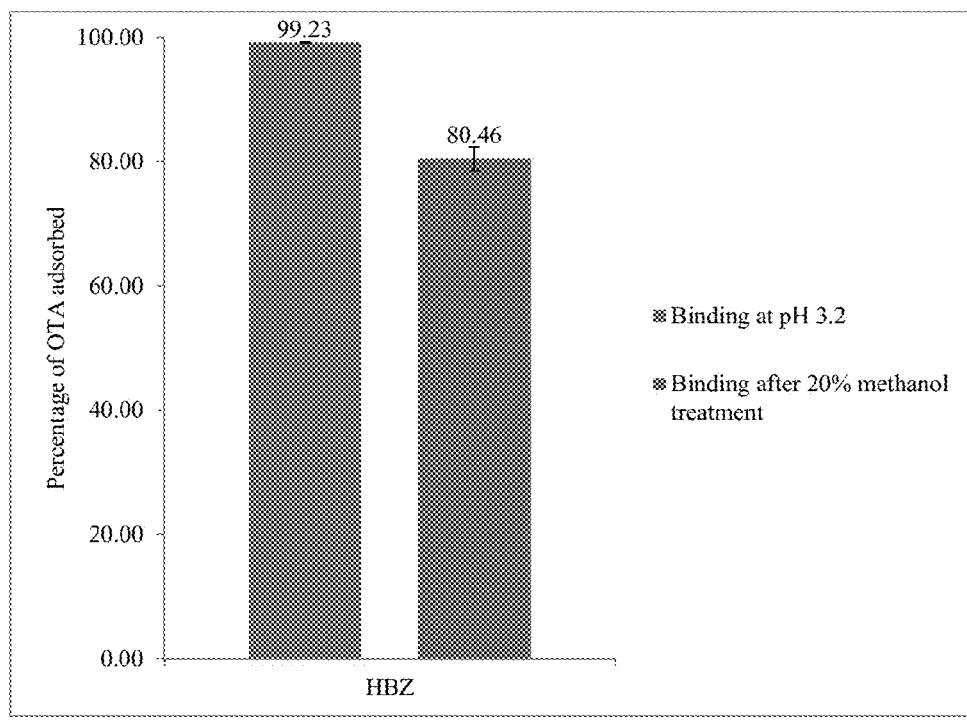
FIG. 7 is a chart on influence of methanol on adsorbed OTA in HBZ Each experimental data represents mean+/−standard error, n=3.

The Chemisorption Index (CI), strength of adsorption of OTA with HBZ was assessed using the method described previously with some modifications (Dwyer M. R., Kubena L., Harvey R. B., Mayura K., Sarr A. B., Buckley S., Bailey R. H. and Phillips T. D. 1997. Effects of Inorganic Adsorbents and Cyclopiazonic Acid in Broiler Chickens. *Poultry Science.* 76: 1141-1149). Briefly, 10 mg of adsorbents were added to 1 ml of water containing 1 μg/ml of OTA ($C_{initial}$) and incubated at 40° C. for 1 hour. After 1 hour, the tubes were centrifuged and the supernatants were analyzed for OTA and the amount of OTA bound was estimated ($C_{bound}$). To the pellet, 1 ml of 20% methanol was added and incubated for 1 hour in shaking water bath, centrifuged and the supernatants were analyzed for OTA ($C_{unbound}$). The percentage of OTA bound to HBZ at each step is shown in FIG. 7. The CI was calculated by using the following Equation 1, $$CI=(C_{Bound}-C_{Unbound})/C_{initial} \quad \text{Equation 1. Chemisorption Index.}$$

The CI results are tabulated in Table 3. CI of HBZ was found to be 0.78. The results suggest that HBZ has the highest propensity and tightest binding for HBZ at the analyzed methanol concentration.

TABLE 3

Assessment of Chemisorption Index (CI) for H-beta zeolite (HBZ).

| | CI |
|---|---|
| Adsorbents | 20% methanol |
| HBZ | 0.78 |

Example 7

Further the experiments were carried out to identify the interactions associated with HBZ and OTA. The interactions associated with HBZ and OTA were evaluated through thermodynamic studies (Avantaggiato, G., Greco, D., Damascelli, A., Solfrizzo, M., and Visconti, A. (2014) Assessment of Multi-mycotoxin Adsorption Efficacy of Grape Pomace. *J. Agric. Food Chem.* 62, 497-507; Ringot, D., Lerzy, B., Bonhoure, J. P., Auclair, E., Oriol, E., and Larondelle, Y. (2005) Effect of temperature on in vitro ochratoxin A biosorption onto yeast cell wall derivatives. *Process. Biochem.:* 3008-3016). The parameters arrived through the thermodynamic studies are: Gibbs free energy change, $\Delta G°$ (kJ/mol), is the fundamental criterion of spontaneity and is given by the Gibbs-Helmholtz equation (Eq.2), $$\Delta G° = -RT \ln K_0 \quad \text{Equation 2. Gibbs-Helmholtz equation.}$$

Where, $K_0$ is the equilibrium constant, R is the universal gas constant and T is the absolute temperature (K).

The equilibrium constant $K_0$ for the adsorption reaction is determined by the Equation 3 where, $Q_{eq}$ (mol/kg) is the molar OTA concentration in adsorbed phase and $C_{eq}$ is the residual OTA concentration in equilibrium (mol/L).

$$K_0 = Q_{eq}/C_{eq} \quad \text{Equation 3. Equilibrium constant.}$$

The constant of equilibrium constant ($K_0$) is expressed in terms of enthalpy and entropy changes is given by Van't Hoff equation (Eq. 4), where R is the universal gas constant, T is the absolute temperature (K), $\Delta H°$ is the enthalpy change (KJ/mol) and $\Delta S°$ is the entropy change (KJ/mol.K). The slope and intercept of the plot of 1/T vs ln $K_0$ were used to calculate $\Delta H°$ and $\Delta S°$ values.

$$\text{Ln } K_0 = (-\Delta H°/RT) + (\Delta S°/R) \quad \text{Equation 4. Van't Hoff equation}$$

The thermodynamic parameters ($\Delta G°$, $\Delta H°$ and $\Delta S°$) for OTA with HBZ was calculated at different temperature (278 K, 288 K, 298 K, 308 K and 318 K) and results are tabulated in Table 4. The negative values of $\Delta G°$ (Table 4) were observed with HBZ which indicates a spontaneous adsorption process. The slope and intercept from the plots of ln K° versus 1/T were used to determine the thermodynamic parameters ($\Delta H°$ and $\Delta S°$) according to the Van't Hoff equation (Table 4). The plots obtained for OTA at experimental temperature conditions gave correlation of $R^2 = 0.9612$ for HBZ (data not shown). The values of $\Delta H°$ (standard enthalpy) and $\Delta S°$ (standard entropy) are shown in Table 4. The negative value of $\Delta H°$ for OTA confirms the exothermic nature of the phenomenon.

The enthalpy was found to be less than 20 KJ/mol, indicating a physisorption phenomenon allowing attaining of the equilibrium rapidly. The magnitude of $\Delta S°$ values also indicates the nature of interactions between adsorbate and adsorbent. HBZ exhibited positive $\Delta S°$ value, suggesting the hydrophobic interaction primarily between adsorbent and adsorbate. In general, enthalpy cost was associated with hydrophobic interactions but reverse in observed with HBZ which suggests the binding also involves polar non-covalent interactions. Negative enthalpy and positive entropy value were also observed with other sorbents (Lin, F.-Y., and Chen, W. Y. (2001) Microcalorimetric Studies on the Interaction Mechanism between Proteins and Hydrophobic Solid Surfaces in Hydrophobic Interaction Chromatography: Effects of Salts, Hydrophobicity of the Sorbent, and Structure of the Protein. *Anal. Chem.* 73: 3875-3883. Ringot, D., Lerzy, B., Bonhoure, J. P., Auclair, E., Oriol, E., and Larondelle, Y. (2005) Effect of temperature on in vitro ochratoxin A biosorption onto yeast cell wall derivatives. *Process. Biochem.* 40: 3008-3016).

TABLE 4

Thermodynamic parameters for OTA adsorption by H-beta zeolite (HBZ).

| Material | Temperature (K) | $K_0$ | In $K_0$ | $\Delta G°$ (KJ/mol) | $\Delta H°$ (KJ/mol) | $\Delta S°$ (KJ/mol · K) |
|---|---|---|---|---|---|---|
| HBZ | 278 | 7592.30 | 8.93 | −20.65 | −14.22 | 22.76 |
|  | 288 | 5424.86 | 8.59 | −20.58 |  |  |
|  | 298 | 4754.36 | 8.46 | −20.97 |  |  |
|  | 308 | 4305.28 | 8.36 | −21.42 |  |  |
|  | 318 | 3244.48 | 8.08 | −21.37 |  |  |

Example 8

Figure 8:
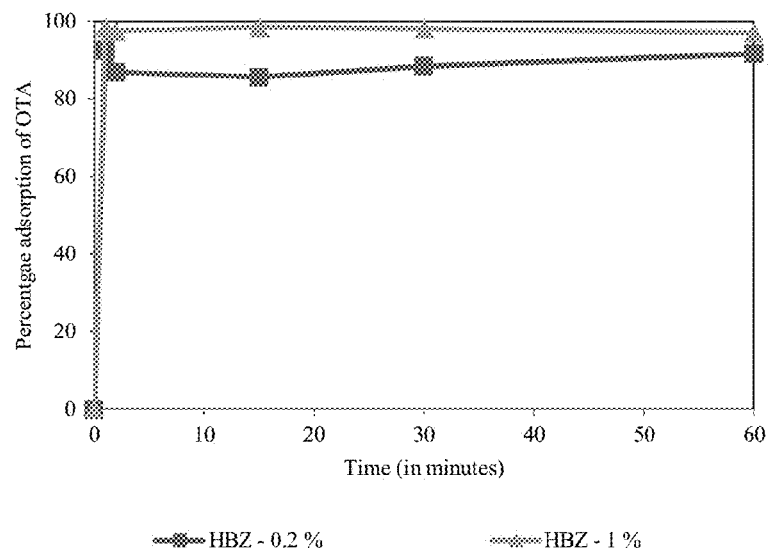
FIG. 8 is a chart on effect of contact time on adsorption rate of OTA by HBZ. Each experimental data represents mean, n=3.

The rate of adsorption of OTA with HBZ was evaluated at various time intervals at pH 6.8 and pH 3.2 individually at 1% w/v (10 mg/ml) as well as 0.2% (2 mg/ml) dosage (triplicate independent experiments) at 1 µg/ml of OTA (Avantaggiato, G., Greco, D., Damascelli, A., Solfrizzo, M., and Visconti, A. (2014) Assessment of Multi-mycotoxin Adsorption Efficacy of Grape Pomace. *J. Agric. Food Chem.* 62: 497-507). Samples were withdrawn at appropriate time intervals (1-60 min). Supernatant liquid portions were analyzed for residual OTA content and the binding percentages were calculated as described in Example 1. The results are shown in FIG. 8.

HBZ was observed with very rapid adsorption of OTA and establishment of equilibrium in a short time. The effect of contact time is of significant importance in mycotoxin reduction by adsorption as most of the major toxins were absorbed very rapidly in the GI tract (Avantaggiato, G., Greco, D., Damascelli, A., Solfrizzo, M., and Visconti, A. (2014) Assessment of Multi-mycotoxin Adsorption Efficacy of Grape Pomace. *J. Agric. Food Chem.* 62: 497-507). OTA is reported to absorb rapidly from the GI tract by passive absorption (Ringot, D., Lerzy, B., Bonhoure, J. P., Auclair, E., Oriol, E., and Larondelle, Y. (2005) Effect of temperature on in vitro ochratoxin A biosorption onto yeast cell wall derivatives. *Process. Biochem.* 40: 3008-3016). The maximum adsorption of >80% was reached within 5 min for HBZ. No rapid change in adsorption percentage was seen after 5 minutes in HBZ. This shows establishment of equilibrium was achieved in a shorter time with HBZ. Such rapid uptake of toxins and establishment of equilibrium by HBZ in short period implies the greater efficacy of material.

Example 9

One of the approaches to estimate the in vivo binding potential of the adsorbents is the analysis of mycotoxin content in excreta receiving adsorbents and comparing it with the control group receiving no adsorbents. The in vivo binding potential of the material was evaluated in broiler birds.

The in vivo excretion trial was done with the six week old Vencobb-400 breed birds. The each study group had six replicates with two birds per replicate. The birds were adapted for five days with ad libitum feed (corn soya based mash feed) and water. Then the birds were starved for 24 hours to empty the gut contents. After the starvation period, each bird was fed with 50 g of feed (contaminated with 200 ppb OTA) of the respective treatment group as shown in Table 5. Water was given ad libitum throughout the trial. The excreta samples were collected for 72 hrs. The collected excreta samples were dried at 50° C. for 48 hours. The OTA in excreta samples were extracted as follows: 5 g of dried excreta samples were extracted with 20 ml of solvent (Acetonirile and 10% glacial acetic acid=1:1) using shaking incubator (Orbitrek, LT) for 60 minutes at 250 revolutions per minute (rpm). After stirring, the mixture was filtered. The filtrate was transferred into a separating funnel and 20 ml hexane) was added, shaken vigorously for 10 minutes and allowed to stand for 10 minutes for the layer separation. The upper hexane layer was discarded to remove fats and oil. The same procedure was repeated twice. The lower layer was further extracted with 50 ml of chloroform thrice. All the chloroform layers were pooled and passed through sodium sulphate bed kept in a funnel. The chloroform was removed using rotary evaporator (Heidolph, Hei-VAP advantage) and the residue was reconstituted in 5 ml of 50% aqueous acetonitrile. The reconstituted layer was centrifuged at 10000 rpm for 10 minute (Eppendorf, 5810R) and the supernatants were quantified by HPLC for OTA as described in Example 1.

TABLE 5

Treatment groups used for the in vivo OTA excretion study. All treatment groups were given OTA# contaminated feed.

| Group | Number of replicates* | HBZ dose (per ton of feed) |
|---|---|---|
| Control | 6 | — |
| Treatment 1 (T1) | 6 | 0.5 kg |
| Treatment 2 (T2) | 6 | 1 kg |

*2 birds/replicate;
200 ppb OTA fortified in mash feed;
HBZ—H-beta zeolite.

Figure 9:
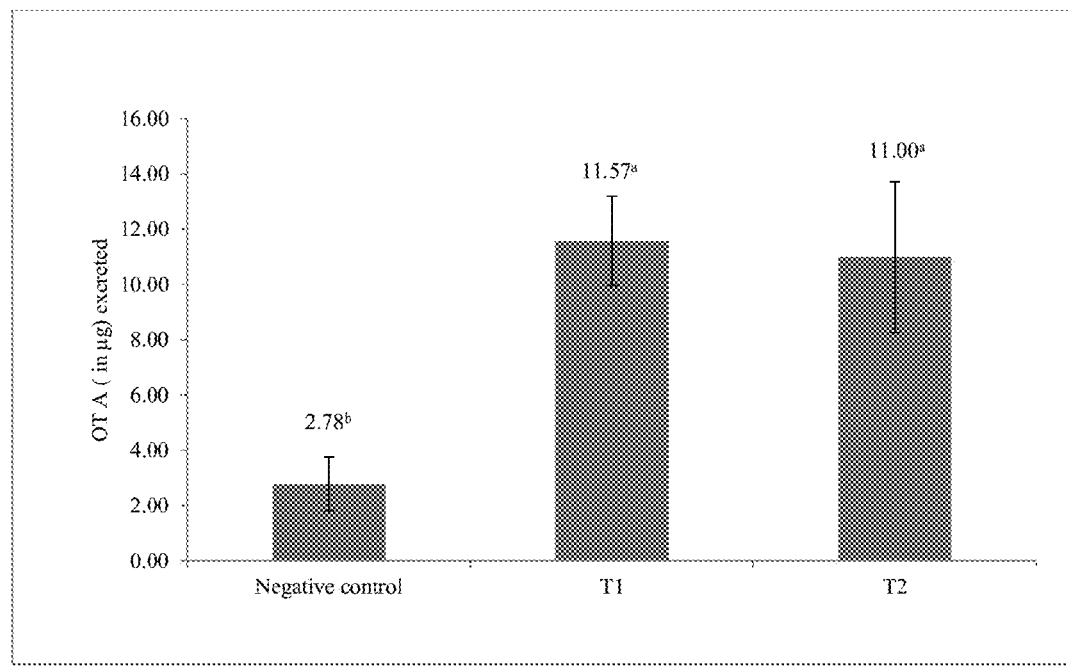
FIG. 9 is a chart of in vivo OTA binding assessment of HBZ. Each experimental data represents mean+/−standard error (n=6 replicates, 2 birds/replicate). Significant difference between the treatment groups were denoted with different letters ($p<0.05$).

The results were presented in FIG. 9. All the treatment groups showed significantly higher amount of OTA in excreta in comparison with control. In this study, the chicken fed on feed spiked with OTA showed significantly higher OTA excreted in all the treatment groups compared to control ($p<0.05$, FIG. 9) which confirms the in vivo binding potential of the material supplemented.

Example 10

Figure 10:
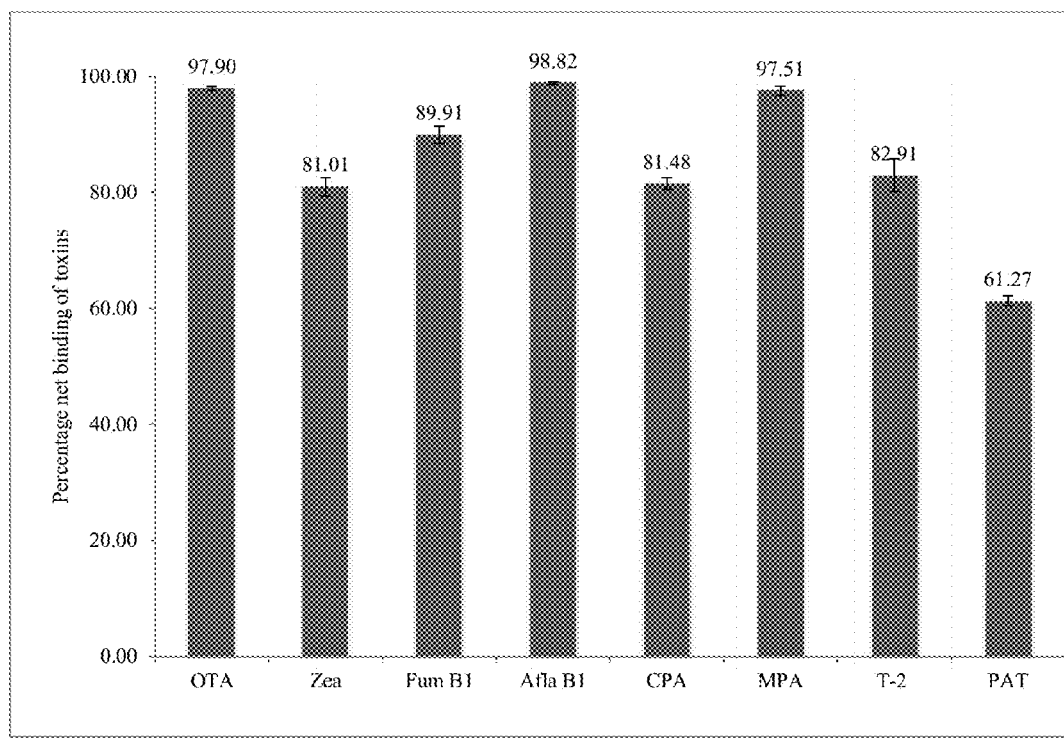
FIG. 10 is a chart of in vitro net binding efficacy of HBZ against mycotoxins. Each experimental data represents mean net binding+/−standard error (n=3).
Figure 13:
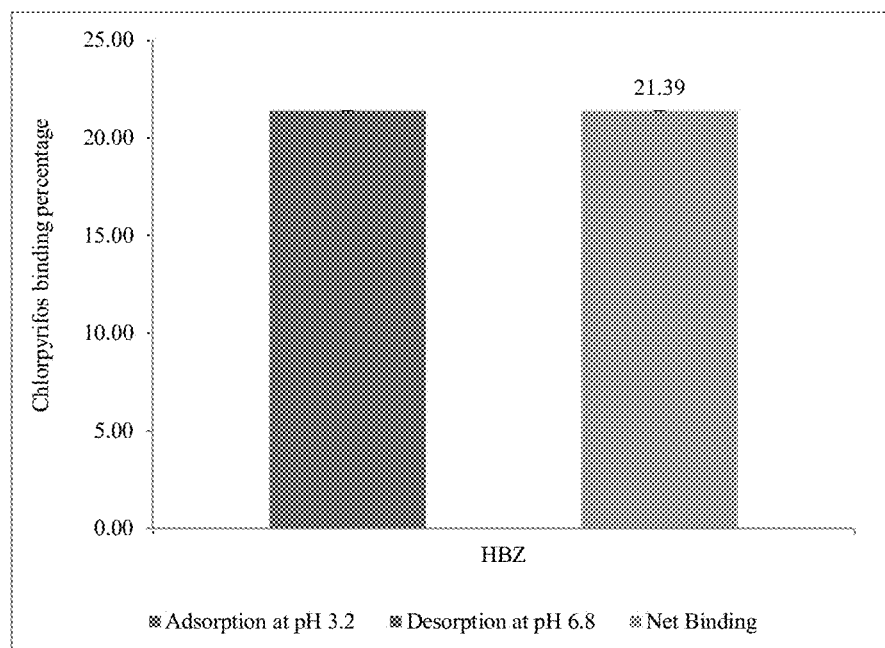
FIG. 13 is a chart on the in vitro binding efficacy of HBZ against chlorpyrifos. Each experimental data represents mean binding+/−standard error (n=3).
Figure 14:
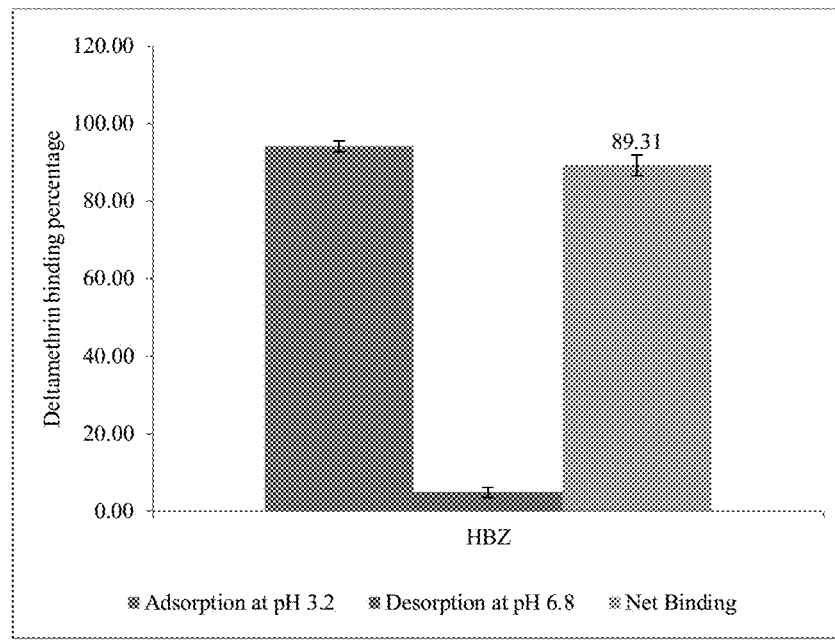
FIG. 14 is a chart on the in vitro binding efficacy of HBZ against deltamethrin. Each experimental data represents mean binding+/−standard error (n=3).

HBZ was further evaluated for its multiple mycotoxins binding property. The stock solutions of mycotoxins were prepared in acetonitrile and stored at 4° C. The working stock solutions (afla B1 (0.5 µg/ml), OTA (1 µg/ml), fum B1 (2 µg/ml), MPA (5 µg/ml), CPA (5 µg/ml), zea (1 µg/ml), PAT (5 µg/ml) and T-2 (2 µg/ml) of individual mycotoxins were prepared in pH 3.2 0.1M citrate buffer as described in Example 1. The biphasic in vitro studies were carried out for the all the mentioned toxins individually as per the procedure briefed in Example 1 and the net binding was calculated. FIG. 10 shows the net toxin binding results of HBZ and the results shows HBZ has multi toxin binding property.

Example 11

Additional experiments were conducted in order to further investigate the in vitro binding of HBZ to adsorb pesticides (carbofuran, thiram, atrazine, deltamethrine, thiamethoxam and chlorpyrifos). The pesticide standards of >98% purity were purchased from Sigma-Aldrich (India).

Chromatographic separation of carbofuran, thiram and chlorpyrifos was achieved by modification of reported methods (Goulart, S. M., Alves, R. D., Neves, A. A., Queiroz, J. H., Assis, T. C. and Queiroz, M. E. L. R. Optimization and validation of liquid-liquid extraction with low temperature partitioning for determination of carbamates in water. Analytica Chimica Acta. 671: 41-47; Bilehal, D. C., Chetti, M. B., Goroji, P. T. and Khethagoudar, M. C. 2012. A Simple, reversed-phase Ultra performance liquid chromatographic method for the simultaneous determination of Monocrotophos, Thiram, carbendazim, Carbaryl and imidacloprid pesticides by Quechers method in chilli samples. International Multidisciplinary Research Journal. 2(9):01-04; Abu-Qare, A. W. and Abou-Donia, M. B. 2001. Determination of Diazinon, Chlorpyrifos, and Their Metabolites in Rat Plasma and Urine by High-Performance Liquid Chromatography. Journal of Chromatographic Science. 39:200-204). The method involved the isocratic mode of separation consisting of 40:60 (v/v) water and acetonitrile at a flow rate of 1.0 mL per minute. The quantification of atrazine, thiamethoxam and deltamethrine was done using the HPLC parameters reported earlier. (Thirumalaiandi, R., Mariappan, P., Ramabhadran, J. 2012. Rapid and Sensitive Analytical Method for Simultaneous Determination of Imidacloprid and Thiamethoxam Residues in Soils of Sugarcane Ecosystem by Reversed-Phase HPLC. Water, Air & Soil Pollution. 223:6045-6050; Trajkovska, v., Petrovska-Jovanovi, s. and Cvetkovski, m. 2000. Development and optimization of a method for the determination of simazine, atrazine and propazine using solid-phase extraction and HPLC/GC. J. Serb. Chem. Soc. 66(3)199-204(2001); Bissacot, D. Z. and Vassilieff, I. 1997. HPLC Determination of Flumethrin, Deltamethrin, Cypermethrin, and Cyhalothrin Residues in the Milk and Blood of Lactating Dairy Cows. Journal of Analytical Toxicology, 21: 397-402.)

Each pesticide sample was injected (20 µL) individually into a reversed-phase monolithic column (Eclipse XB-C18, 150 mm×4.6 mm i.d., 5 µm, Agilent), connected to a Shimadzu LC-20AD HPLC system coupled to a diode array detector. The wavelengths used for quantification were 272 nm, 210 nm, and 280 nm for carbofuran, thiram and chlorpyrifos respectively. The chromatograms were processed through LC solution (ver 1.25) software.

The stock solutions (100 ppm) of pesticides were prepared in acetonitrile and stored at 4° C. The desired concentration of working standard solution of pesticides was prepared by the use of a pipette to transfer the required volume of stock solution into a volumetric flask and then purged with nitrogen to remove the solvent. Then a small volume of buffer (0.1 M citrate buffer, pH 3.2) was added, vortexed, and made up to final volume using the same buffer. The prepared working standard solution was directly used for the binding assay. The pesticides (carbofuran, thiram, chlorpyrifos, deltamethrin, atrazine and thiamethoxam) working concentration of 1 µg/mL was used for the binding assay—

The ability of HBZ to bind pesticides was evaluated through biphasic in vitro method as described in Example 1. The binding assay was conducted for all pesticides, and was repeated independently three times.

The efficacy of HBZ to bind carbofuran, thiram, chlorpyrifos, deltamethrin, thiamethoxam and atrazine are shown in FIG. 11, FIG. 12 FIG. 13, FIG. 14, FIG. 15 and FIG. 16 respectively. The results shows that HBZ could able to bind most of the pesticides effectively which are commonly observed in animal feeds.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. An animal feed composition comprising animal feed; and beta zeolite in either a $NH_4+$ or $H+$ form, wherein the beta zeolite animal feed supplement is present in an amount effective at binding pesticides present in animal feed; wherein the pesticide is selected from the group consisting of carbofuran, thiram, deltamethrin, atrazine and thiamethoxam; and said animal feed composition having a beta zeolite concentration of at least 0.5% by weight.

2. The animal feed composition of claim 1, wherein the animal feed is suitable for monogastric or ruminant animals.

3. The animal feed composition of claim 1 having a beta zeolite concentration of at least 1% by weight.

4. The animal feed composition of claim 1, wherein the beta zeolite is in the $NH_4+$ form.

5. A method of preparing an animal feed composition for monogastric or ruminant animals that is effective at binding pesticides selected from the group consisting of carbofuran, thiram, deltamethrin, atrazine and thiamethoxam comprising adding beta zeolite in either a $NH_4+$ or $H+$ form to animal feed, wherein said animal feed composition having a beta zeolite concentration of at least 0.5% by weight.

* * * * *